US012607617B2

(12) United States Patent
   Chu et al.

(10) Patent No.:  US 12,607,617 B2
(45) Date of Patent:      Apr. 21, 2026

(54) WATER QUALITY MONITORING DEVICE AND MONITORING METHOD THEREOF

(71) Applicant: Industrial Technology Research Institute, Hsinchu (TW)

(72) Inventors: Chen-Hua Chu, Hsinchu County (TW); Chun-Kuo Liu, Hsinchu City (TW); Yi-Hong Liu, Taoyuan City (TW); Chi-Fan Wang, Taoyuan City (TW); Jung-Hao Wang, Hsinchu County (TW); Sheng-Wei Peng, Hsinchu County (TW); Yu-Xuan Lin, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 1139 days.

(21) Appl. No.: 17/561,729

(22) Filed: Dec. 24, 2021

(65) Prior Publication Data

US 2023/0204558 A1      Jun. 29, 2023

(51) Int. Cl.
   *G01N 33/18*       (2006.01)
   *G01N 21/31*       (2006.01)
       (Continued)

(52) U.S. Cl.
   CPC ......... *G01N 33/1806* (2013.01); *G01N 21/31* (2013.01); *G01N 21/33* (2013.01);
       (Continued)

(58) Field of Classification Search
   CPC .... G01N 33/1806; G01N 21/31; G01N 21/33; G01N 21/3577; G01N 21/51;
       (Continued)

(56) References Cited

U.S. PATENT DOCUMENTS 10,551,311 B2      2/2020   Smith et al.
11,194,074 B2 *   12/2021   DiFoggio ............... G06V 10/30
       (Continued)

FOREIGN PATENT DOCUMENTS

CN         101655462      2/2010
CN         201503394      6/2010
       (Continued)

OTHER PUBLICATIONS

Pai, Tzu-Yi, et al. "Grey and neural network prediction of suspended solids and chemical oxygen demand in hospital wastewater treatment plant effluent." Computers & Chemical Engineering 31.10 (2007): 1272-1281. (Year: 2007).*
       (Continued)

*Primary Examiner* — Dominic J Bologna
(74) *Attorney, Agent, or Firm* — JCIPRNET

(57)       ABSTRACT

A water quality monitoring device and a monitoring method thereof are provided. The water quality monitoring device includes a water tank, a first and a second optical detection devices and a control circuit. The water tank has an accommodating space to carry a liquid. The first optical detection device provides a first light to detect and obtain a first reference light intensity, a first scattered light intensity, and a first penetrating light intensity. The second optical detection device provides a second light to detect and obtain a second reference light intensity, a second scattered light intensity, and a second penetrating light intensity. The control circuit calculates a water quality detection value of the liquid based on the first reference light intensity, the first scattered light intensity, the first penetrating light intensity, the second reference light intensity, the second scattered light intensity, and the second penetrating light intensity.

11 Claims, 7 Drawing Sheets

(51) Int. Cl.

| | | |
|---|---|---|
| *G01N 21/33* | (2006.01) | |
| *G01N 21/3577* | (2014.01) | |
| *G01N 21/51* | (2006.01) | |
| *G01N 21/90* | (2006.01) | |
| *G01N 21/94* | (2006.01) | |

(52) U.S. Cl.
CPC ......... *G01N 21/3577* (2013.01); *G01N 21/51* (2013.01); *G01N 21/90* (2013.01); *G01N 21/94* (2013.01); *G01N 33/18* (2013.01); *G01N 33/1826* (2013.01); *G01N 2201/121* (2013.01)

(58) Field of Classification Search
CPC ........ G01N 21/90; G01N 21/94; G01N 33/18; G01N 33/1826; G01N 2201/121
See application file for complete search history.

(56) References Cited

U.S. PATENT DOCUMENTS

| | | |
|---|---|---|
| 2003/0025909 A1 | 2/2003 | Hallstadius |
| 2009/0022218 A1 | 1/2009 | Kim et al. |
| 2013/0169949 A1 | 7/2013 | Liaw et al. |
| 2020/0124526 A1* | 4/2020 | Kono ..................... G01N 21/51 |
| 2020/0209208 A1* | 7/2020 | Li ....................... H01L 25/0753 |
| 2024/0085395 A1* | 3/2024 | Wang ..................... G01J 3/021 |

FOREIGN PATENT DOCUMENTS

| | | |
|---|---|---|
| CN | 102384901 | 3/2012 |
| CN | 102798602 | 11/2012 |
| CN | 204142624 | 2/2015 |
| CN | 107643260 | 1/2018 |
| CN | 109655110 | 4/2019 |
| CN | 209589841 | 11/2019 |
| CN | 111292418 | 6/2020 |
| CN | 111650141 | 9/2020 |
| CN | 215066128 | 12/2021 |
| TW | 200639392 | 11/2006 |
| TW | 201003068 | 1/2010 |
| TW | 201124711 | 7/2011 |
| TW | M413120 | 10/2011 |
| TW | 456185 | 10/2014 |
| TW | 503531 | 10/2015 |
| TW | 201942562 | 11/2019 |
| WO | 2013185620 | 12/2013 |

OTHER PUBLICATIONS

Raposo, F., et al. "Assessment of a modified and optimised method for determining chemical oxygen demand of solid substrates and solutions with high suspended solid content." Talanta 76.2 (2008): 448-453. (Year: 2008).*

Lorena Parra et al., "Design and development of low cost smart turbidity sensor for water quality monitoring in fish farms", Aquacultural Engineering, vol. 81, Feb. 2018, pp. 10-18.

Zhang Zhen-Nan et al., " Research of Water Turbidity Detection Device Based on Dual-channel Two-dimensional Photoelectric Detection", Instrument Technique and Sensor, Issue 5, May 2017, with English abstract, pp. 45-48.

Youchao Wang et al., "Low-cost Turbidity Sensor for Low-power Wireless Monitoring of Fresh-Water Courses" , IEEE Sensors Journal , vol. 18, Issue 11, Jun. 2018, pp. 1-8.

Shanqing Zhang et al., "Development of Chemical Oxygen Demand On-Line Monitoring System Based on a Photoelectrochemical Degradation Principle", Environmental Science & Technology, vol. 40, Issue 7, Feb. 2006, pp. 2363-2368.

G. Cazaudehore et al., "Determination of chemical oxygen demand of agricultural wastes by combining acid hydrolysis and commercial COD kit analysis", Journal of Environmental Management, vol. 250, Sep. 2019, pp. 1-5.

"Office Action of Taiwan Counterpart Application", issued on Sep. 5, 2022, p. 1-p. 7.

Cheng; Yin et al., "Optical Signal Detecting and Processing For Water Quality Measurement System by Ultraviolet Absorption Spectrum", Journal of Atmospheric and Environmental Optics, Sep. 2009, with English abstract, pp. 393-400, vol. 4, No. 5.

Wang; Chunmei et al., "Full-Spectrum Analysis for Online Monitoring of Chemical Oxygen Demand in Water Quality", Silicon Valley, 2014, with English abstract, pp. 1-3, vol. 22, No. 166.

"Office Action of China Counterpart Application", issued on Jul. 12, 2025, p. 1-p. 10.

* cited by examiner

WATER QUALITY MONITORING DEVICE AND MONITORING METHOD THEREOF

TECHNICAL FIELD

The disclosure relates to a fluid monitoring technology, and more particularly, to a water quality monitoring device and a monitoring method thereof.

BACKGROUND

With development of industrialization, water pollution problem has become increasingly sever. For specific industries (such as fish farming, wastewater discharge, water resource management, etc.), it is necessary to monitor water quality conditions in real time and accurately in order to detect problems and avoid loss immediately.

Most of the water quality monitoring devices arranged on site measure water quality by directly contacting water. If the water quality monitoring device is arranged in a harsh environment, the measurement quality of the water quality sensor is likely to be unstable. Moreover, for different water quality monitoring technologies, there might be a variety of interfering substances in water body in harsh environments, and the water quality measurement results will be dramatically affected. Some water quality monitoring technologies use chemicals to pre-treat the water body to remove interfering substances roughly. However, this approach not only requires additional costs for chemicals, but also requires regular maintenance of such water quality monitoring devices. On the other hand, the water quality monitoring device needs response time when measuring the water body, so it is difficult to provide water quality information in real time.

In light of the above, it is desired that the water quality sensor still can achieve stable quality in water quality measurement in harsh environments, which is a goal pursued by practitioners in current water quality monitoring technology.

SUMMARY

The water quality monitoring device of the disclosure includes a water tank, a first optical detection device, a second optical detection device, and a control circuit. The water tank has an accommodating space to carry a liquid. The first optical detection device includes a first light emitter, a first reference light receiver, a first scattered light receiver and a first penetrating light receiver. The first light emitter provides a first light. The first light is incident into the accommodating space of the water tank. The first reference light receiver detects the light intensity of the first light before the first light is incident into the accommodating space, so as to obtain the first reference light intensity. The first scattered light receiver receives the scattered light in the first light through the accommodating space of the water tank to detect and obtain the first scattered light intensity of the first light. The first penetrating light receiver receives the penetrating light in the first light through the accommodating space of the water tank to detect and obtain the first penetrating light intensity of the first light. The second optical detection device includes a second light emitter, a second reference light receiver, a second scattered light receiver, and a second penetrating light receiver. The second light emitter provides a second light, and the first light and the second light have different wavelengths. The second light is incident into the accommodating space of the water tank. The second reference light receiver detects the light intensity of the second light before the second light is incident into the accommodating space, so as to obtain the second reference light intensity. The second scattered light receiver receives the scattered light in the second light through the accommodating space of the water tank to detect and obtain the second scattered light intensity of the second light. The second penetrating light receiver receives the penetrating light in the second light through the accommodating space of the water tank to detect and obtain the second penetrating light intensity of the second light. The control circuit is electrically coupled to the first optical detection device and the second optical detection device, and calculates a water quality detection value of the liquid based on the first reference light intensity, the first scattered light intensity, the first penetrating light intensity, the second reference light intensity, the second scattered light intensity, and the second penetrating light intensity.

The water quality monitoring method of the disclosure adopts the water quality monitoring device for water quality monitoring, and the water quality monitoring method includes the following steps. The first light is provided to detect and obtain the first reference light intensity, the first scattered light intensity, and the first penetrating light intensity. The second light is provided to detect and obtain the second reference light intensity, the second scattered light intensity, and the second penetrating light intensity. The water quality detection value of the liquid is calculated based on the first reference light intensity, the first scattered light intensity, the first penetrating light intensity, the second reference light intensity, the second scattered light intensity and the second penetrating light intensity.

Based on the above, the water quality monitoring device and the monitoring method thereof in the embodiment of the disclosure utilize the optical detection device to cooperate with the reference light receiver, and utilize the water quality monitoring algorithm with light source correction to instantly correct the measurement error caused by light source intensity change of the light emitter. In this way, it is possible to avoid unstable quality in water quality measurement due to shift of light source intensity. In addition, the embodiment of the disclosure has multiple groups of light emitters, and is equipped with a water quality monitoring algorithm with multi-component compensation, which can contribute to instantly eliminate specific interfering substances from complex water body, and solve the problem that a single light source device cannot eliminate the influence brought by interfering substances in complex water body on measurement results.

DETAILED DESCRIPTION OF DISCLOSED EMBODIMENTS

Figure 1:
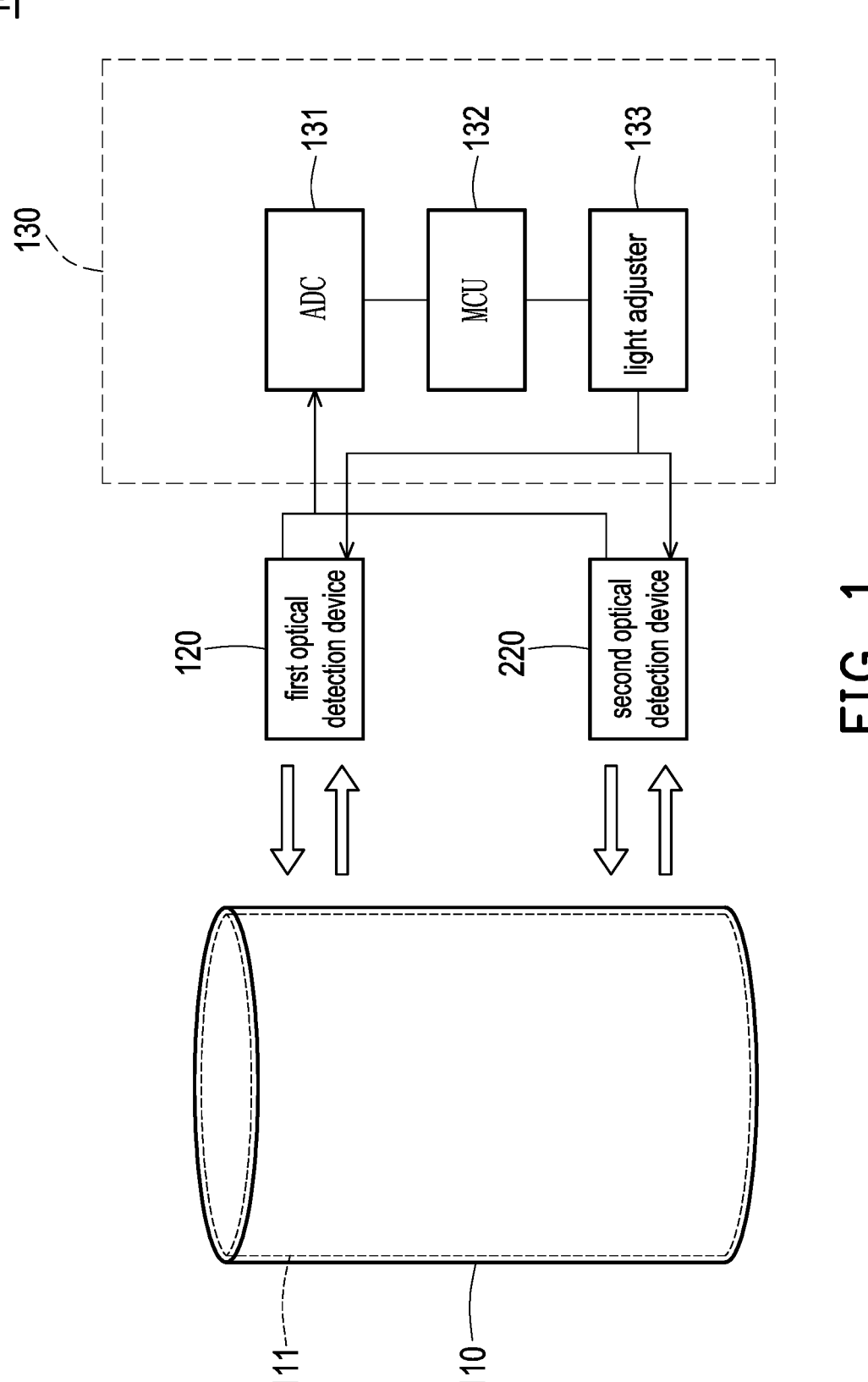
FIG. 1 is a schematic view of a water quality monitoring device according to an embodiment of the disclosure.

FIG. 1 is a schematic view of a water quality monitoring device 100 according to an embodiment of the disclosure. The water quality monitoring device 100 mainly includes a water tank 110, a first optical detection device 120, a second optical detection device 220 and a control circuit 130. The water tank 110 is provided with an accommodating space 111 to carry a liquid. The first optical detection device 120 detects the water quality of the liquid in the water tank 110 by a first light L1, and the second optical detection device 220 detects the water quality of the liquid in the water tank 110 by a second light L2. The control circuit 130 is electrically coupled to the first optical detection device 120 and the second optical detection device 220. The water quality monitoring device 100 uses two or more sets of optical detection devices to simultaneously measure various substances at different wavelengths, thereby establishing the optical properties of various substances in complex water body, and combined with a water quality monitoring algorithm with multi-component compensation, which can contribute to instantly eliminate specific interfering substances from complex water body, and solve the problem that the water quality monitoring device with a single wavelength light source cannot eliminate the influence brought by interfering substances in complex water body on measurement results. In this way, water quality detection results can be estimated or calculated more accurately, and the disclosure has the advantage of simultaneously monitoring multiple components in the water body.

Figure 2:
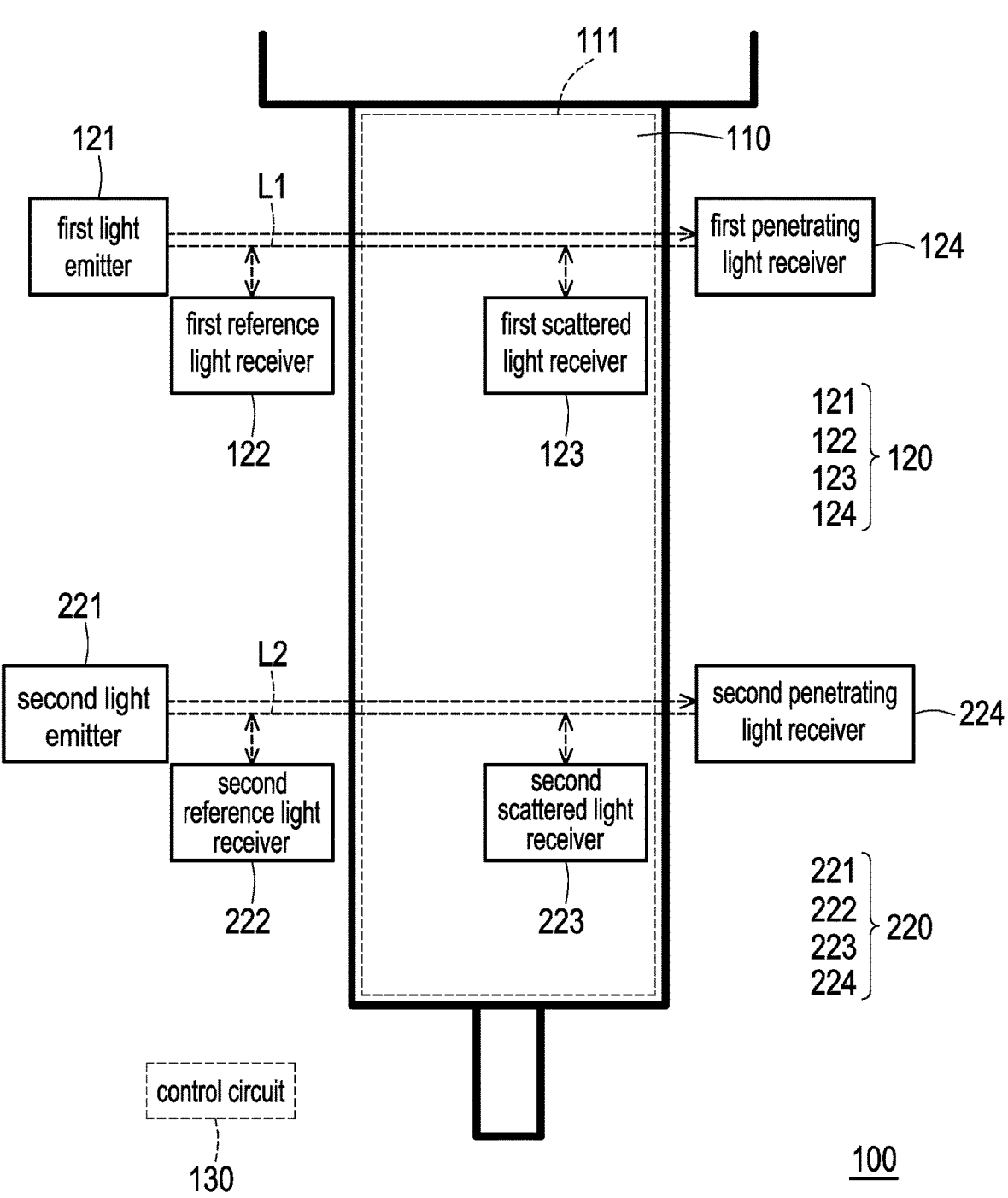
FIG. 2 is a schematic side view of the configuration of various components in an optical detection device according to an embodiment of the disclosure.

FIG. 2 is a schematic side view of the configuration of various components in an optical detection device according to an embodiment of the disclosure. The first optical detection device 120 includes a first light emitter 121, a first reference light receiver 122, a first scattered light receiver 123 and a first penetrating light receiver 124. The first light emitter 121 provides the first light L1 which is incident into the accommodating space 111 of the water tank 110. The second optical detection device 220 includes a second light emitter 221, a second reference light receiver 222, a second scattered light receiver 223 and a second penetrating light receiver 224. The functions of the components in the second optical detection device 220 are similar to those of the components in the first optical detection device 120. The second light emitter 221 provides the second light L2 which is incident into the accommodating space 111 of the water tank 110. The first light emitter 121 and/or the second light emitter 221 in this embodiment use a convex lens to condense light, and light emitters that use different technologies to condense light can also be applied to this embodiment according to actual needs. The first light emitter 121 and/or the second light emitter 221 has a light emission end, and the light emission end in this embodiment refers to the position of the lens tip of the first light emitter 121 and/or the second light emitter 221 for emitting the first light L1 and/or second light L2.

The first reference light receiver 122 detects the light intensity of the first light L1 before the first light L1 is incident into the accommodating space 111 of the water tank 110 to obtain the first reference light intensity Ir1. In detail, the first reference light receiver 122 has a detection end, and the detection end in this embodiment refers to the position of the lens tip in the first reference light receiver 122 for detecting the first light L1. It is suggested that the first reference light receiver 122 should be close to the first light emitter 121 to obtain a good detection result. In addition, it is suggested that the detection end (i.e., the lens tip in the first reference light receiver 122 used for detecting the first light L1) of the first reference light receiver 122 in this embodiment should be close to the transmission path of the first light L1. For example, the detection end of the first reference light receiver 122 is within 1 cm from the light emission end of the first light emitter 121; or the detection end of the first reference light receiver 122 is within 5 mm from the vertical distance of the optical axis of the first light L1.

The first scattered light receiver 123 receives the scattered light in the first light L1 through the accommodating space 111 of the water tank 110 to detect and obtain the first scattered light intensity Is1. The first penetrating light receiver 124 receives the penetrating light in the first light L1 through the accommodating space 111 of the water tank 110 to detect and obtain the first penetrating light intensity It1.

Similarly, the second reference light receiver 222 detects the light intensity of the second light L2 before the second light L2 is incident into the accommodating space 111 to obtain the second reference light intensity Ir2. The second scattered light receiver 223 receives the scattered light in the second light L2 through the accommodating space 111 of the water tank 110 to detect and obtain the second scattered light intensity Is2 of the second light L2. The second penetrating light receiver 224 receives the penetrating light in the second light L2 through the accommodating space 111 of the water tank 110 to detect and obtain the second penetrating light intensity It2. The control circuit 130 calculates the water quality detection value of the liquid based on the first reference light intensity Ir1, the first scattered light intensity Is1, the first penetrating light intensity It1, the second reference light intensity Ir2, the second scattered light intensity Is2 and the second penetrating light intensity It2. In an embodiment, the water quality detection value may be one of the concentration of CODs and the concentration of dissolved organic carbon (DOC).

It should be noted that the wavelength of the second light L2 in the second optical detection device 200 is different from the wavelength of the first light L1 in the first optical detection device 120, so that the water quality monitoring device 100 can accurately obtain water quality detection results, and the advantage of monitoring multiple components in the water body can be achieved simultaneously. The first light emitter 121 in this embodiment may be a visible light emitter or an infrared light emitter, that is, the first light L1 may be a light in a visible light band or an infrared light band. In an embodiment, when the first light L1 is in the visible light band, it can be applied to turbidity measurement of a transparent water body in the water tank 110. When the first light L1 is in the infrared light band, it can be simultaneously applied to turbidity measurement of the transparent or colored water body in the water tank 110. In addition, the second light emitter 221 in this embodiment may be an ultraviolet light emitter, that is, the second light L2 may be a light in the ultraviolet wavelength band.

Due to the long-term use of the water quality monitoring device 100, the heating of a lamp source, or environmental temperature factors and many other problems, the first light L1 and the second light L2 emitted by the first light emitter 121 and the second light emitter 221 might be interfered when being incident into the accommodating space 111 of the water tank 110, resulting in unstable intensities of the first light L1 and the second light L2. As a result, an error occurs in the subsequent calculation of the water quality detection value. Therefore, in this embodiment, the first reference light receiver 122 and the second reference light receiver 222 are added to instantly correct the light source intensities of the first light L1 and the second light L2, thereby enhancing the accuracy of water quality detection through the water quality monitoring algorithm. In this way, it is possible to avoid drift or instability of light source intensity of the water quality monitoring device 100 caused by the environment or other factors, thus avoiding poor reproducibility of the water quality detection.

Figure 3:
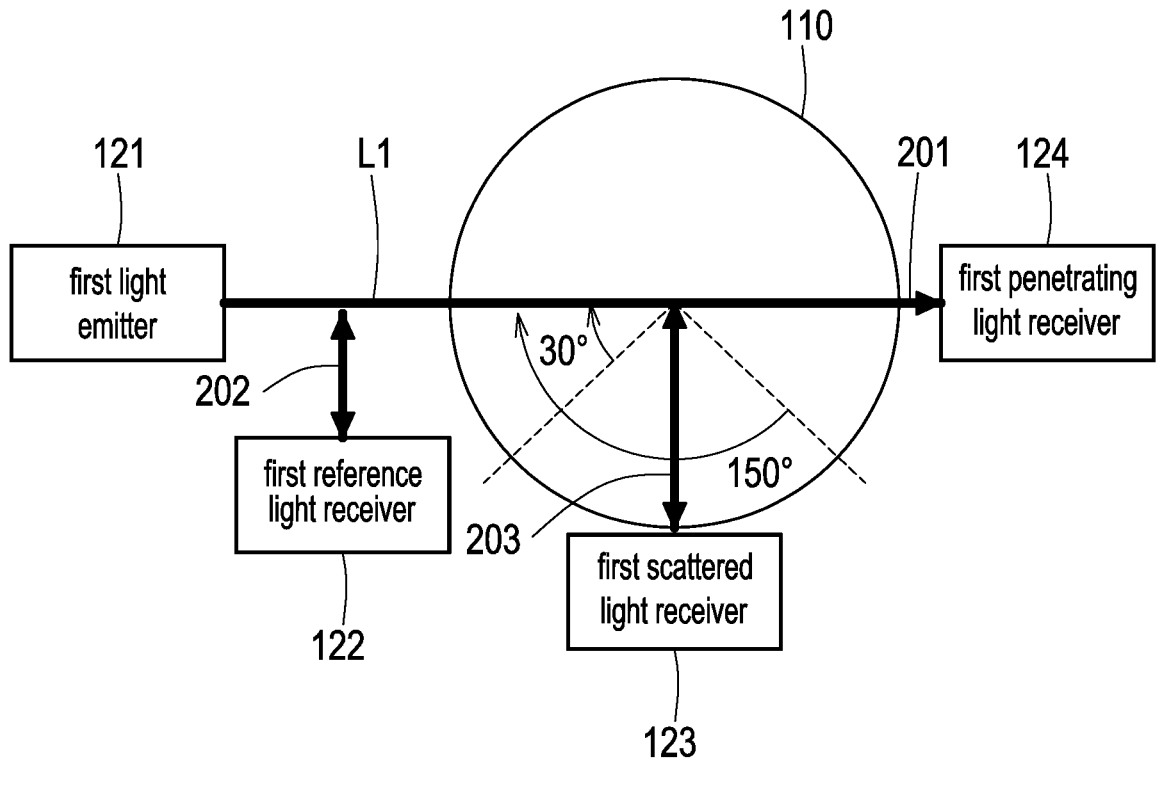
FIG. 3 is a schematic view illustrating relative positions of various components in the first optical detection device and the water tank according to an embodiment of the disclosure.

FIG. 3 is a schematic view illustrating relative positions of various components in the first optical detection device 120 and the water tank 110 according to an embodiment of the disclosure. It should be noted that although the first optical detection device 120 is used as an example in this embodiment, it should be noted that the relative positions of various components in the second optical detection device 220 and the water tank 110 are similar to the first optical detection device 120. Therefore, no repetition is incorporated herein. FIG. 3 shows the relative positions of the water tank 110 on the XY plane formed by the axis X and the axis Y in FIG. 2 and the first light emitter 121, the first reference light receiver 122, the first scattered light receiver 123 and the first penetrating light receiver 124 in the first optical detection device 120 while other components are omitted. The first light emitter 121 emits the first light L1. The first light L1 is incident into the accommodating space 111 of the water tank 110 in an incident direction 201.

The first reference light receiver 122 is adapted to detect the light intensity of the first light L1 in the ambient air before being incident into the water tank 110 to obtain the first reference light intensity Ir1. Therefore, in this embodiment, the detection end of the first reference light receiver 122 is disposed between the first light emitter 121 and the water tank 110, so that the first reference light receiver 122 can detect the intensity of the first light L1 before the first light L1 is incident into the accommodating space 111, thereby obtaining the first reference light intensity Ir1. The detection end of the first reference light receiver 122 has a reference light detection direction 202. Moreover, an angle between the incident direction 201 in this embodiment and the reference light detection direction 202 of the first reference light receiver 122 is 90 degrees. In this way, the present embodiment uses the reference light receiver 122 to detect the light source intensity of the first light L1 in real time, thereby enhancing the accuracy of water quality detection.

When the first light L1 passes through the accommodating space 111 of the water tank 110, a part of the first light L1 will have an optical effect due to the suspended matter of the liquid in the accommodating space 111 or the refractive index of the liquid itself, so that a part of the first light L1 (referred to as the penetrating light of the first light L1) can penetrate the liquid and be detected by the first penetrating light receiver 124 to obtain the first penetrating light intensity It1. Another part of the first light L1 (referred to as the scattered light of the first light L1) is detected by the first scattered light receiver 123 due to the scattering effect, so as to obtain the scattered light intensity.

In detail, the detection end of the first scattered light receiver 123 has a scattered light detection direction 203. For different substances to be detected in the water quality, the scattering angle of the first light L1 affected by the liquid will also be different. Therefore, those applying this embodiment can adjust the value of the angle between the incident direction 201 and scattered light detection direction 203 of the first scattered light receiver 123 according to their needs. In this embodiment, the angle between the incident direction 201 of the first light L1 and the scattered light detection direction 203 of the first scattered light receiver 123 may be one of 30 degrees to 150 degrees, for example, 45 degrees, 90 degrees or 135 degrees, but not limited thereto. The first scattered light receiver 123 receives the scattered light in the first light L1 through the accommodating space 111 of the water tank 110 to detect and obtain the first scattered light intensity Is1 of the first light L1. On the other hand, the first optical detection device 120 can also increase the number of the first scattered light receiver 123 according to needs, so as to obtain the water quality detection result more accurately.

The first penetrating light receiver 124 is adapted to detect part of the first light L1 (i.e., the penetrating light in the first light L1) after penetrating the accommodating space 111 of the water tank 110. Therefore, the angle between the incident direction 201 of the first light L and the detection direction of the first penetrating light receiver 124 is 180 degrees. The first penetrating light receiver 124 receives the penetrating light in the first light L1 through the accommodating space 111 of the water tank 110 to detect and obtain the first penetrating light intensity It1 of the first light L1.

Please refer to FIG. 1, the control circuit 130 of this embodiment may include an analog-to-digital converter (ADC) 131, a micro control unit (MCU) 132 and a light adjuster 133. The ADC 131 is coupled to the first optical detection device 120 and the second optical detection device 220 respectively, and the ADC 131 converts the analog light intensity signals in the first optical detection device 120 and the second optical detection device 220 into digital light intensity signals. The MCU 132 is coupled to the ADC 131, and the MCU 132 calculates the water quality detection result through the captured digital light intensity signal and the water quality monitoring algorithm. That is to say, the MCU 132 calculates water quality detection values of liquid based on the first reference light intensity Ir1, the first scattered light intensity Is1, the first penetrating light intensity It1, the second reference light intensity Ir2, the second scattered light intensity Is2 and second penetrating light intensity It2. The light adjuster 133 is coupled to the MCU 132 and can control and adjust the light intensity of the first light L1 and/or the second light L2 emitted by the first light emitter 121 and/or the second light emitter 221 in the first optical detection device 120 and/or the second optical detection device 220 according to the parameter settings of the MCU 132.

Figure 4:
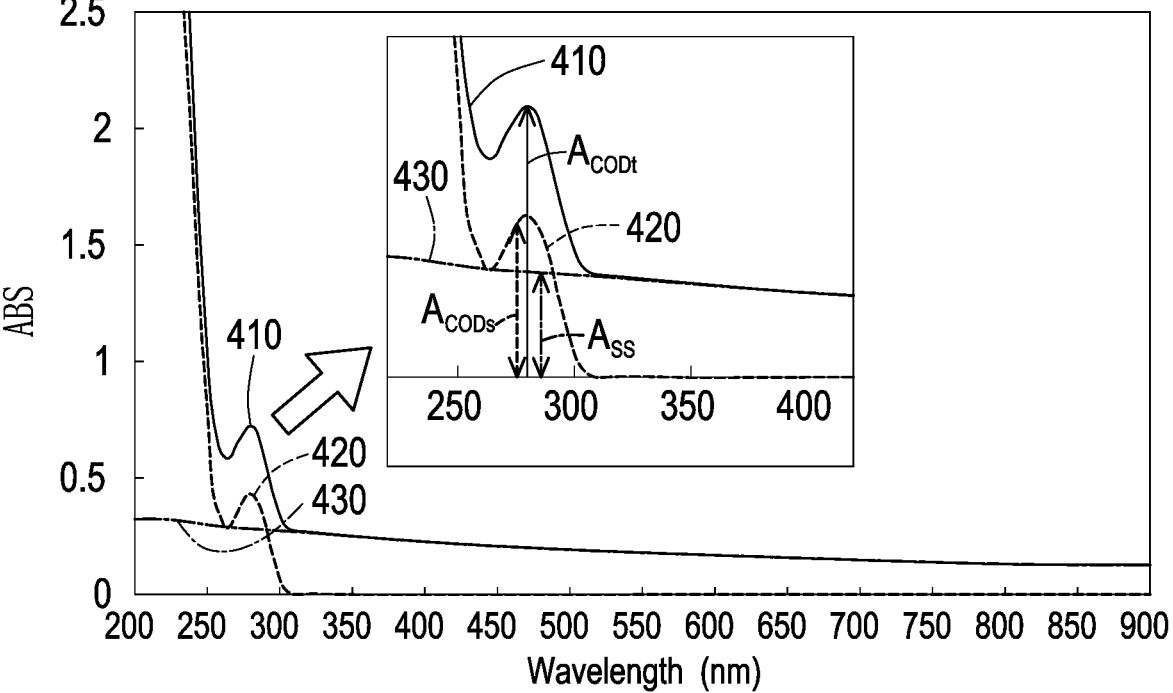
FIG. 4 is a light absorbance characteristic map of total chemical oxygen demand (CODt), soluble chemical oxygen demand (CODs) and suspended solid (SS) of a liquid.

FIG. 4 is a light absorbance characteristic map of CODt 410, CODs 420 and SS 430 in the liquid. The light absorbance of CODs 420 responds to exposure to light with wavelengths approximately below 305 nm, the light absorbance of SS 430 responds to exposure to light with full wavelength, and the light absorbance of CODt 410 includes contributions from CODs 420 and SS 430. Therefore, when illuminated by light of a specific wavelength (e.g., 200-305 nm), the light absorbance $A_{CODt}$ of CODt 410 is the sum of the light absorbance $A_{CODs}$ of CODs 420 and the light absorbance $A_{SS}$ of SS 430. For ease of explanation, the light absorbance $A_{CODt}$ of CODt 410, the light absorbance $A_{CODs}$ of CODs 420 and the light absorbance $A_{SS}$ of SS 430 in FIG. 4 are located at slightly different wavelength positions, but it should be indicated that in fact the three light absorbances $A_{CODt}$, $A_{CODs}$ and $A_{SS}$ are located at the same wavelength position and perform the aforementioned calculations. On the other hand, the light absorbance $A_{CODt}$ of CODt 410 can be calculated by measuring through ultraviolet light (corresponding to the second light L2), and the light absorbance $A_{SS}$ of SS 430 can be calculated by measuring through visible light or infrared light (corresponding to the first light L1). Therefore, the light absorbance $A_{CODs}$ of the CODs 420 can be calculated through multi-wavelength light by the water quality monitoring device 100 of this embodiment.

Figure 5:
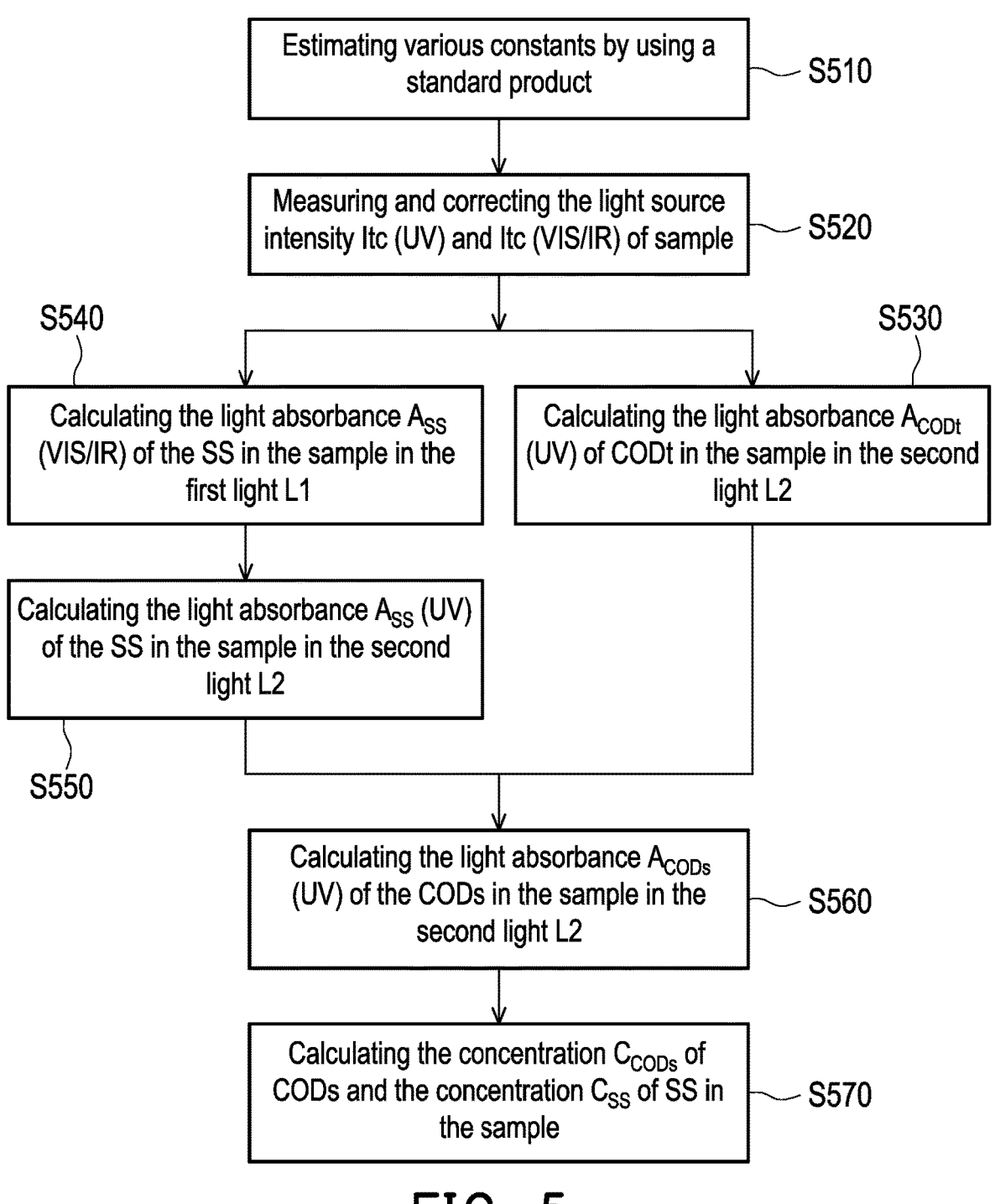
FIG. 5 is a flow chart of calculating CODs and SS of a liquid according to a water quality monitoring algorithm with multi-component compensation according to an embodiment of the disclosure.

FIG. 5 is a flow chart of calculating CODs and SS of a liquid according to a water quality monitoring algorithm with multi-component compensation according to an embodiment of the disclosure. Referring to FIG. 2 and FIG. 5 both, in this embodiment, the first light L1 may be visible light or infrared light, which is represented by "VIS/IR" in the following embodiments. In detail, visible light can be any continuous or single wavelength light within a wavelength of 400 to 750 nm, and infrared light can be any continuous or single wavelength light within a wavelength of 750 to 950 nm. The second light L2 is ultraviolet light, which is represented by "UV" in the following embodiments. Ultraviolet light can be any continuous or single wavelength light within a wavelength of 200 to 400 nm.

In step S510 of FIG. 5, the present embodiment utilizes chemical oxygen demand (COD) and SS standards (e.g., a configured standardized liquid) to make the control circuit 130 evaluate various constants, such as the initial value It0 (VIS/IR) of the first penetrating light intensity of the first light L1, the initial value It0 (UV) of the second penetrating light intensity of the second light L2, the light absorbance coefficient $K_{SS}$ (VIS/IR) of SS of the first light L1, the light absorbance coefficient $K_{SS}$ (UV) of SS of the second light L2 and the light absorbance coefficient $K_{CODs}$ (UV) of CODs.

In step S520, the control circuit 130 measures and corrects the light intensity Itc (VIS/IR) corresponding to the first light L1 and the light intensity Itc (UV) corresponding to the second light L2 of the liquid which serves as the sample in the accommodating space 111 of the water tank 110 through the first optical detection device 120 and the second optical detection device 220. The Itc (VIS/IR) is a correction value of the first penetrating light intensity, which is obtained by correcting the first penetrating light intensity It1 through the first reference light intensity Ir1, and the first penetrating light intensity It1 is obtained by the first penetrating light receiver 124 after the first light L1 penetrates the sample. The Itc (UV) is a correction value of the second penetrating light intensity, which is obtained by correcting the second penetrating light intensity It2 through the second reference light intensity Ir2, and the second penetrating light intensity It2 is obtained by the second penetrating light receiver 224 after the second light L2 penetrates the sample.

In detail, the MCU 132 in the control circuit 130 has some predefined constants, that is, the initialized first reference light intensity preset value Irc1 corresponding to the first reference light receiver 122 and the initialized second reference light intensity preset value Irc2 corresponding to the second reference light receiver 222. Then, the first reference light receiver 122 detects the first light L1 to obtain the first reference light intensity Ir1; the first penetrating light receiver 124 detects the penetrating light of the first light L1 to obtain the first penetrating light intensity It1; the second reference light receiver 222 detect the second light L2 to obtain the second reference light intensity Ir2; the second penetrating light receiver 224 detects the penetrating light of the second light L2 to obtain the second penetrating light intensity It2. The MCU 132 obtains the various light intensities through the ADC 131, and calculates the first reference light intensity correction ratio (Rr1=Ir1/Irc1), the first penetrating light intensity correction value (Itc (VIS/IR)=It1/Rr1), the second reference light intensity correction ratio (Rr2=Ir2/Irc2), and the second penetrating light intensity correction value (Itc (UV)=It2/Rr2) based on the light intensities. In short, the control circuit 130 calculates the first penetrating light intensity correction value Itc (VIS/IR) according to the first reference light intensity preset value Irc1, the first reference light intensity Ir1 and the first penetrating light intensity It1, and also calculates the second penetrating light intensity correction value Itc (UV) according to the second reference light intensity preset value Irc2, the second reference light intensity Ir2 and the second penetrating light intensity It2.

The control circuit 130 can respectively calculate the light absorbance $A_{CODt}$ (UV) of CODt in the sample in the second light L2 (step S530) and the light absorbance $A_{SS}$ (VIS/IR) of the SS in the sample in the first light L1 (step S540) according to the aforementioned constants.

In this embodiment, in step S530, the light absorbance $A_{CODt}$ (UV) of CODt of the liquid in the second light L2 is calculated according to the initial value It0 (UV) of the second penetrating light intensity and the corrected second penetrating light intensity corresponding to the second light L2 (i.e., the correction value Itc (UV) of the second penetrating light intensity), and the equation (1) is as follows:

$$A_{CODt}(UV) = \log\left[\frac{It0(UV)}{Itc(UV)}\right] \tag{1}$$

In this embodiment, in step S540, the light absorbance $A_{SS}$ (VIS/IR) of SS of the liquid in the first light L1 is calculated according to the initial value It0 (VIS/IR) of the first penetrating light intensity and the corrected first penetrating light intensity corresponding to the first light L1 (i.e., the correction value Itc (VIS/IR) of the first penetrating light intensity), and the equation (2) is as follows:

$$A_{SS}(VIS/IR) = \log\left[\frac{It0(VIS/IR)}{Itc(VIS/IR)}\right] \tag{2}$$

In step S550, the control circuit 130 further uses the constants to calculate the light absorbance $A_{SS}$ (UV) of the SS in the sample in the second light L2.

In this embodiment, in step S550, the light absorbance $A_{SS}$ (UV) of SS in the sample in the second light L2 is calculated according to the light absorbance coefficient $K_{SS}$ (VIS/IR) of the first light L1, the light absorbance coefficient $K_{SS}$ (UV) of SS of the second light L2, and the light absorbance $A_{SS}$ (VIS/IR) of the SS in the sample in the first light L1, and the equation (3) is as follows:

$$A_{SS}(UV) = \left[\frac{K_{SS}(UV)}{K_{SS}(VIS/IR)}\right] \times A_{SS}(VIS/IR) \tag{3}$$

9           10

In step S560, the control circuit 130 can deduct the calculation result of step S550 (that is, the light absorbance $A_{SS}$ (UV) of the SS in the sample in the second light L2) from the calculation result of step S530 (that is, the light absorbance $A_{CODt}$ (UV) of CODt in the sample in the second light L2) to calculate the light absorbance $A_{CODs}$ (UV) of the CODs in the sample in the second light L2.

In the present embodiment, the equation (4) of calculating light absorbance $A_{CODs}$ (UV) in step S560 is as follows:

$$A_{CODs}(UV) = A_{CODt}(UV) - A_{SS}(UV) \qquad (4)$$

In step S570, the control circuit 130 utilizes the calculation result of step S560 (i.e., $A_{CODs}$ (UV)), $K_{CODs}$ (UV) and the measurement optical path (i.e., the transmission path of light in the accommodating space 111 of the water tank 110) to calculate the concentration $C_{CODs}$ of CODs in the sample, and the calculation result of step S540 (i.e., $A_{SS}$ (VIS/IR)), $K_{SS}$ (VIS/IR) and the measurement optical path can also be used to calculate the concentration $C_{SS}$ of SS in the sample.

In this embodiment, in step S570, the equations (5) and (6) of calculating the concentration $C_{CODs}$ of CODs in the sample and the concentration $C_{SS}$ of SS in the sample are as follows:

$$C_{CODs} = \frac{A_{CODs}(UV)}{[K_{CODs}(UV) \times \text{optical path}]} \qquad (5)$$

$$C_{SS} = \frac{A_{SS}(VIS/IR)}{[K_{SS}(VIS/IR) \times \text{optical path}]} \qquad (6)$$

Figure 6:
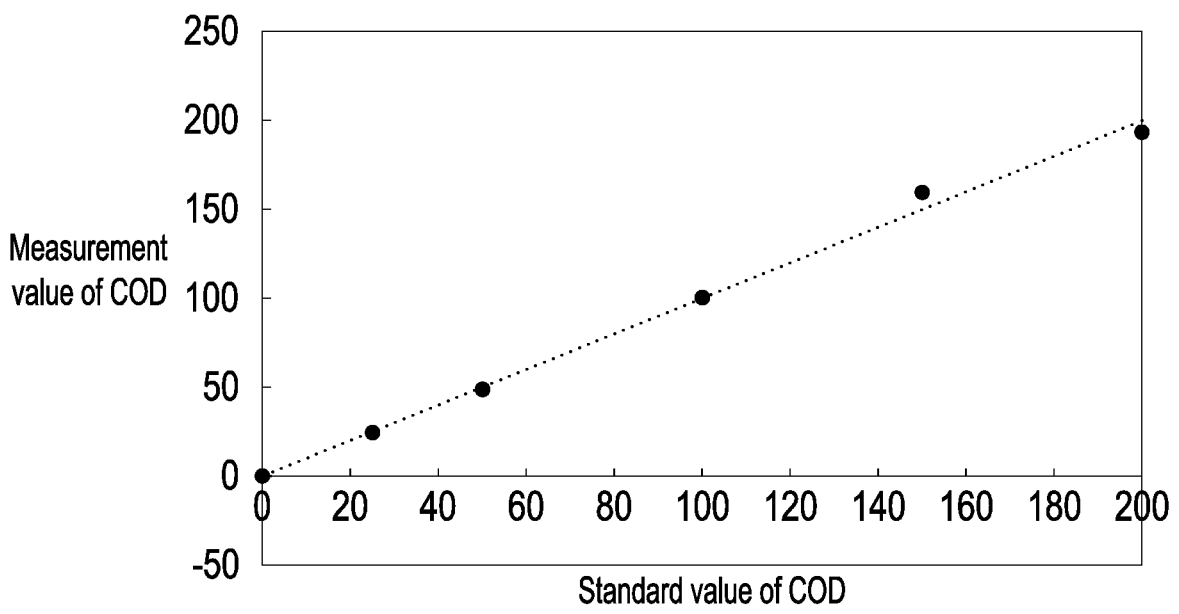
FIG. 6 and FIG. 7 are curve diagrams respectively showing comparisons of COD measurement value and COD standard value as well as SS measurement value and SS standard value through analysis on standard product of different concentrations by utilizing the water quality monitoring device of the present embodiment and standard method used by laboratory.
Figure 7:
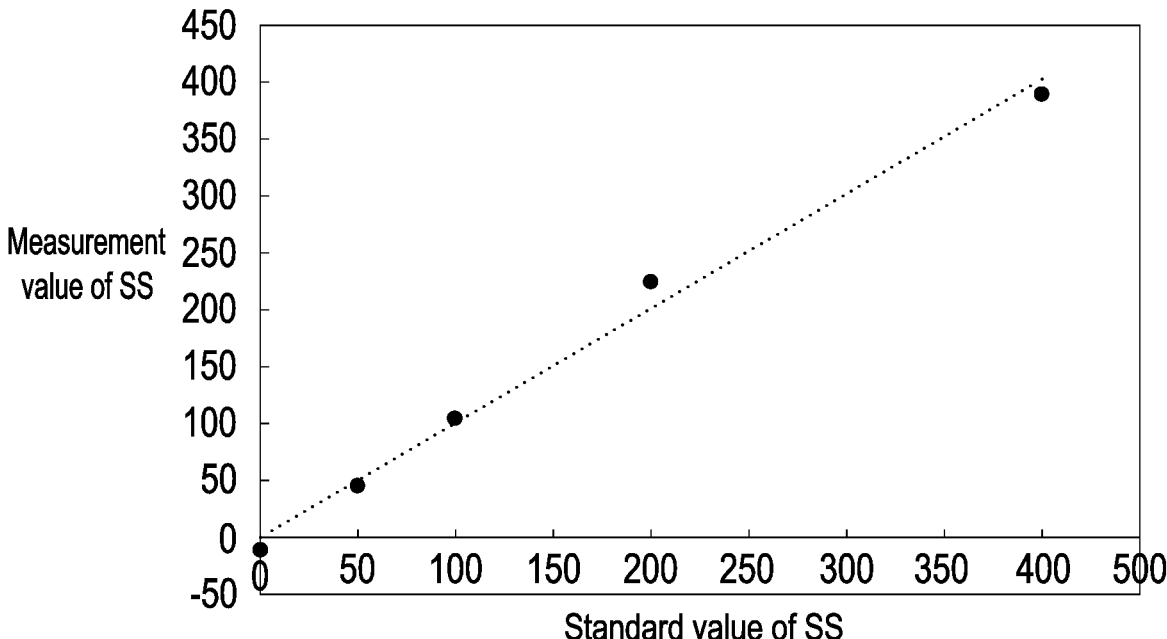

The water quality monitoring device 100 with multi-band light source in the present embodiment is utilized to estimate COD and SS with the aforementioned standard product, and the method is compared with the standard method used by laboratory. It can be found that the optical COD and optical SS measured by the present embodiment are very close to the theoretical COD value and theoretical SS value measured by standard method used by laboratory. FIG. 6 and FIG. 7 are curve diagrams respectively showing comparisons of COD measurement value and COD standard value as well as SS measurement value and SS standard value through analysis on standard product of different concentrations by utilizing the water quality monitoring device 100 of the present embodiment and standard method used by laboratory. Please refer to FIG. 6 and FIG. 7, if the COD standard value and the SS standard value obtained by the standard method used by laboratory are used as the horizontal axis, and the measurement result of the water quality monitoring device 100 of this embodiment (that is, the COD measurement value and the SS measurement value) is used as the vertical axis for comparison, the slope between the COD measurement value and the COD standard value or the slope between the SS measurement value and the SS standard value is about 0.99 to 1.01, and there is a very high correlation between the two, that is, the determination coefficient $R^2$ is greater than 0.99.

Figures 8, 9:
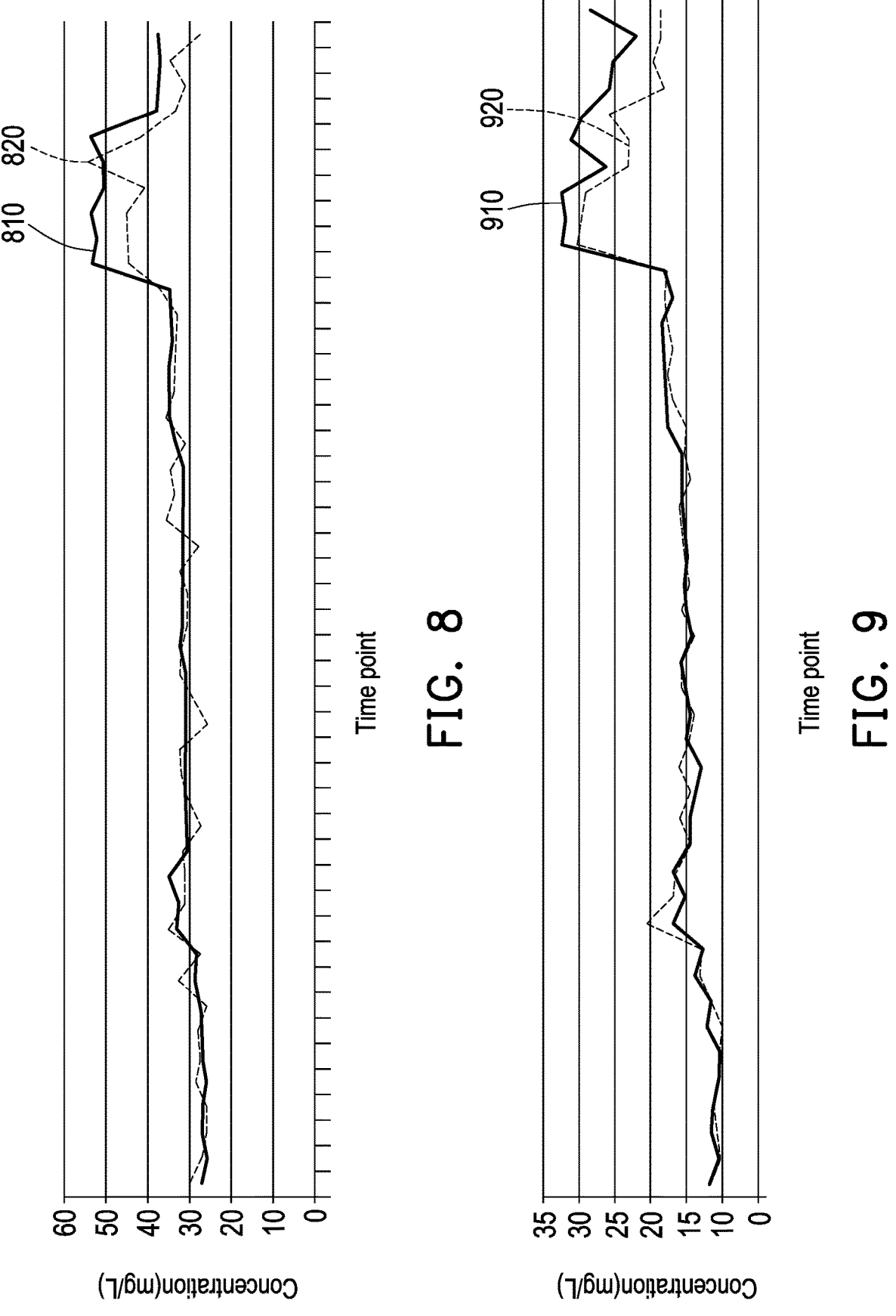
FIG. 8 and FIG. 9 are respectively curve diagrams showing comparison between CODs and SS by continuously monitoring the sample using the water quality monitoring device of the present embodiment and the standard method used by laboratory.

FIG. 8 and FIG. 9 are respectively curve diagrams showing comparison between CODs and SS by continuously monitoring the sample using the water quality monitoring device 100 of the present embodiment and the standard method used by laboratory. The horizontal axis of FIG. 8 and FIG. 9 represents the time point at which the water quality detection device in the present embodiment performs operation, and the vertical axis represents the concentration values of CODs and SS respectively, and the unit of measurement is mg/L.

The curve 810 of FIG. 8 is the numerical curve of CODs measured by the water quality detection device of the present embodiment, and the curve 820 is the numerical curve of CODs concentration measured by the standard method used by laboratory. Comparing the curves 810 and 820, it can be seen that the error between the CODs value measured by the water quality detection device in this embodiment and the CODs concentration measured by the standard method used by laboratory is less than or equal to 11%, that is, the CODs value measured by the water quality detection device in the present embodiment is close to the CODs value measured by the standard method used by laboratory.

The curve 910 of FIG. 9 is the numerical curve of SS measured by the water quality detection device of the present embodiment, and the curve 920 is the numerical curve of SS concentration measured by the standard method used by laboratory. Comparing the curves 910 and 920, it can be seen that the error between the SS value measured by the water quality detection device in this embodiment and the SS concentration measured by the standard method used by laboratory is less than or equal to 20%, that is, the SS value measured by the water quality detection device in the present embodiment is close to the SS value measured by the standard method used by laboratory.

Based on the above, the water quality monitoring device and the monitoring method thereof according to the embodiment of the present disclosure utilize the optical detection device to cooperate with the reference light receiver, and utilize the water quality monitoring algorithm with light source correction to instantly correct the measurement error caused by the light source intensity change of the light emitter. As such, it is possible to avoid the instability of water quality measurement caused by the drift of light source intensity, while mitigating the influence of interfering substances in complex water body on the measurement results, so as to estimate or calculate the water quality detection results more accurately. In addition, the embodiment of the present disclosure simultaneously measures multiple substances at different wavelengths, establishes the optical properties of various substances in complex water body, and combined with a water quality monitoring algorithm with multi-component compensation, which can contribute to instantly eliminate the specific interfering substances in complex water body.

What is claimed is:

1. A water quality monitoring device, comprising:
a water tank, having an accommodating space to carry a liquid;
a first optical detection device, comprising:
a first light emitter, providing a first light, wherein the first light is incident into the accommodating space of the water tank;
a first reference light receiver, detecting a light intensity of the first light before the first light is incident into the accommodating space, so as to obtain a first reference light intensity;
a first scattered light receiver, receiving a scattered light in the first light through the accommodating space of the water tank to detect and obtain a first scattered light intensity of the first light; and
a first penetrating light receiver, receiving a penetrating light in the first light through the accommodating space of the water tank to detect and obtain a first penetrating light intensity of the first light;
a second optical detection device, comprising:

a second light emitter, providing a second light, wherein the second light is incident into the accommodating space of the water tank, and the first light and the second light have different wavelengths;

a second reference light receiver, detecting a light intensity of the second light before the second light is incident into the accommodating space, so as to obtain a second reference light intensity;

a second scattered light receiver, receiving a scattered light in the second light through the accommodating space of the water tank to detect and obtain a second scattered light intensity of the second light; and a second penetrating light receiver, receiving a penetrating light in the second light through the accommodating space of the water tank to detect and obtain a second penetrating light intensity of the second light; and a control circuit, electrically coupled to the first optical detection device and the second optical detection device, wherein the control circuit calculates a water quality detection value of the liquid based on the first reference light intensity, the first scattered light intensity, the first penetrating light intensity, the second reference light intensity, the second scattered light intensity, and the second penetrating light intensity;

wherein the control circuit is further configured to:

estimate an initial value of the first penetrating light intensity of the first light, an initial value of the second penetrating light intensity of the second light, a light absorbance coefficient of chemical oxygen demand (COD) of the second light, a light absorbance coefficient of suspended solid (SS) of the first light and a light absorbance coefficient of SS of the second light by using a standard product;

measure and correct the first penetrating light intensity corresponding to the first light and the second penetrating light intensity corresponding to the second light in the liquid;

calculate a light absorbance of total chemical oxygen demand (CODt) in the liquid in the second light according to the initial value of the second penetrating light intensity and the corrected second penetrating light intensity corresponding to the second light;

calculate a light absorbance of SS in the liquid in the first light according to the initial value of the first penetrating light intensity and the corrected first penetrating light intensity corresponding to the first light, and calculate a light absorbance of the SS in the liquid in the second light according to the light absorbance coefficient of the SS of the first light, the light absorbance coefficient of the SS of the second light and the light absorbance of the SS in the liquid in the first light;

deduct the light absorbance of the SS in the liquid in the second light from the light absorbance of the CODt in the liquid in the second light to calculate a light absorbance of CODs in the liquid in the second light; and calculate a concentration of the CODs in the liquid according to the light absorbance of the CODs in the liquid in the second light, the light absorbance coefficient of the COD of the second light and a measurement optical path, or calculating a concentration of the SS in the liquid according to the light absorbance of the SS in the liquid in the first light, the light absorbance coefficient of the SS of the first light and the measurement optical path.

2. The water quality monitoring device according to claim 1, wherein the water quality detection value is one of a concentration of a soluble chemical oxygen demand (CODs) and a concentration of a dissolved organic carbon (DOC).

3. The water quality monitoring device according to claim 1, wherein the first light is incident into the accommodating space of the water tank in an incident direction, and an angle between the incident direction and a detection direction of the first penetrating light receiver is 180 degrees, an angle between the incident direction and a reference light detection direction of the first reference light receiver is 90 degrees, and an angle between the incident direction and a scattered light detection direction of the first scattered light receiver is one of 30 degrees to 150 degrees.

4. The water quality monitoring device according to claim 1, wherein the second light is incident into the accommodating space of the water tank in an incident direction, and an angle between the incident direction and a detection direction of the second penetrating light receiver is 180 degrees, an angle between the incident direction and a reference light detection direction of the second reference light receiver is 90 degrees, and an angle between the incident direction and a scattered light detection direction of the second scattered light receiver is one of 30 degrees to 150 degrees.

5. The water quality monitoring device according to claim 1, wherein the first reference light receiver comprises a detection end, and the detection end is within 1 cm from a light emission end of the first light emitter.

6. The water quality monitoring device according to claim 1, wherein the second reference light receiver comprises a detection end, and the detection end is within 1 cm from a light emission end of the second light emitter.

7. The water quality monitoring device according to claim 1, wherein the first reference light receiver comprises a detection end, and the detection end is within 5 mm from a vertical distance of an optical axis of the first light.

8. The water quality monitoring device according to claim 1, wherein the second reference light receiver comprises a detection end, and the detection end is within 5 mm from a vertical distance of an optical axis of the second light.

9. The water quality monitoring device according to claim 1, wherein the first light emitter is a visible light emitter or an infrared light emitter, and the second light emitter is an ultraviolet light emitter.

10. A water quality monitoring method using the water quality monitoring device claimed in claim 1 for monitoring water quality, and the water quality monitoring method comprising:

providing the first light to detect and obtain the first reference light intensity, the first scattered light intensity, and the first penetrating light intensity;

providing the second light to detect and obtain the second reference light intensity, the second scattered light intensity, and the second penetrating light intensity; and calculating the water quality detection value of the liquid based on the first reference light intensity, the first scattered light intensity, the first penetrating light intensity, the second reference light intensity, the second scattered light intensity and the second penetrating light intensity;

wherein the step of calculating the water quality detection value of the liquid based on the first reference light intensity, the first scattered light intensity, the first penetrating light intensity, the second reference light intensity, the second scattered light intensity and the second penetrating light intensity comprises:

estimating an initial value of the first penetrating light intensity of the first light, an initial value of the second penetrating light intensity of the second light, a light absorbance coefficient of chemical oxygen demand (COD) of the second light, a light absorbance coefficient of suspended solid (SS) of the first light and a light absorbance coefficient of SS of the second light by using a standard product;

measuring and correcting the first penetrating light intensity corresponding to the first light and the second penetrating light intensity corresponding to the second light in the liquid;

calculating a light absorbance of total chemical oxygen demand (CODt) in the liquid in the second light according to the initial value of the second penetrating light intensity and the corrected second penetrating light intensity corresponding to the second light;

calculating a light absorbance of SS in the liquid in the first light according to the initial value of the first penetrating light intensity and the corrected first penetrating light intensity corresponding to the first light, and calculating a light absorbance of the SS in the liquid in the second light according to the light absorbance coefficient of the SS of the first light, the light absorbance coefficient of the SS of the second light and the light absorbance of the SS in the liquid in the first light;

deducting the light absorbance of the SS in the liquid in the second light from the light absorbance of the CODt in the liquid in the second light to calculate a light absorbance of CODs in the liquid in the second light; and calculating a concentration of the CODs in the liquid according to the light absorbance of the CODs in the liquid in the second light, the light absorbance coefficient of the COD of the second light and a measurement optical path, or calculating a concentration of the SS in the liquid according to the light absorbance of the SS in the liquid in the first light, the light absorbance coefficient of the SS of the first light and the measurement optical path.

11. The water quality monitoring method according to claim 10, wherein the control circuit has an initialized first reference light intensity preset value corresponding to the first reference light receiver and an initialized second reference light intensity preset value corresponding to the second reference light receiver, and the step of measuring and correcting the first penetrating light intensity corresponding to the first light and the second penetrating light intensity corresponding to the second light in the liquid further comprises:

calculating a correction value of the first penetrating light intensity according to the first reference light intensity preset value, the first reference light intensity, and the first penetrating light intensity; and calculating a correction value of the second penetrating light intensity according to the second reference light intensity preset value, the second reference light intensity, and the second penetrating light intensity.

* * * * *